United States Patent [19]

Fecht et al.

[11] Patent Number: 4,617,019
[45] Date of Patent: Oct. 14, 1986

[54] CATHETER

[75] Inventors: David C. Fecht, Manchester; Thomas W. Davison, Chesterfield, both of Mo.

[73] Assignee: Sherwood Medical Company, St. Louis, Mo.

[21] Appl. No.: 655,853

[22] Filed: Sep. 28, 1984

[51] Int. Cl.⁴ ............................................. A61M 25/00
[52] U.S. Cl. ..................................... 604/280; 604/274
[58] Field of Search .................................. 604/43–45, 604/264, 274, 280–284

[56] References Cited

U.S. PATENT DOCUMENTS

| | | |
|---|---|---|
| 1,879,249 | 9/1932 | Honsaker . |
| 2,972,779 | 2/1961 | Cowley ................................. 18/48 |
| 3,064,651 | 11/1962 | Henderson ........................ 604/274 |
| 3,190,290 | 6/1965 | Alley et al. ........................ 128/348 |
| 3,295,527 | 1/1967 | Alley et al. ........................ 604/280 |
| 3,625,793 | 12/1971 | Sheridan et al. ................ 604/101 X |
| 3,656,486 | 4/1972 | Robertson ........................ 128/349 R |

FOREIGN PATENT DOCUMENTS 0069861  4/1982  Japan ................................... 604/280

Primary Examiner—Dalton L. Truluck
Attorney, Agent, or Firm—Stanley N. Garber; Andrew J. Beck; William R. O'Meara

[57] ABSTRACT

An intercostal catheter is provided which, when the distal end is flattened for insertion into an incision of a patient from the exterior, has a distal end that is smooth and substantially free of deleterious protuberances to minimize damage the patient. A method of making an intercostal catheter is provided that includes the steps of severing tubing at an acute angle to its longitudinal axis, and displacing a portion of the proximal extremity of the end wall of the severed end to prevent the occurrence of a protuberance when the tube end is flattened for insertion.

17 Claims, 11 Drawing Figures

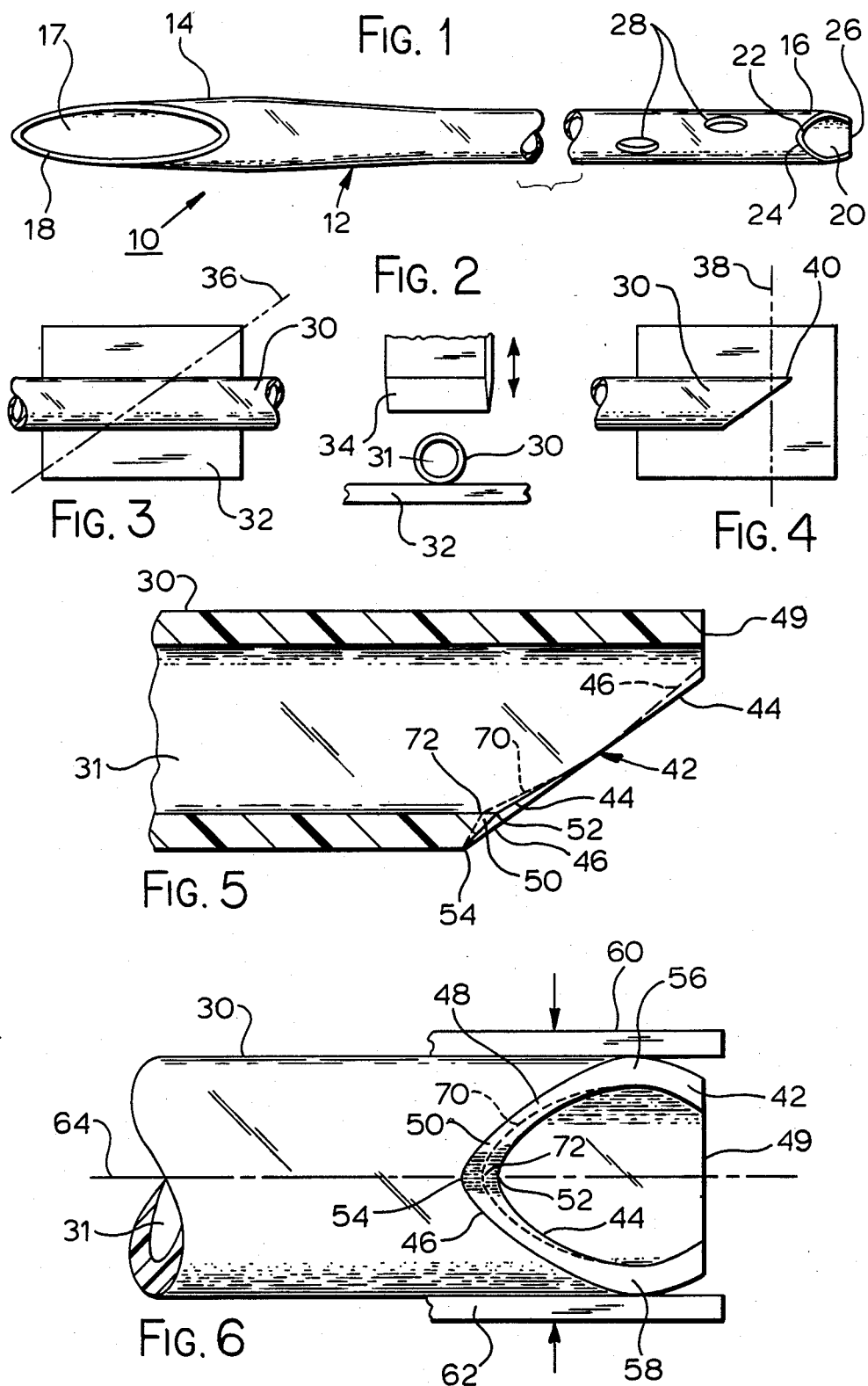

CATHETER

TECHNICAL FIELD

This invention relates to catheters and more particularly to an intercostal catheter and to the method of making the same.

BACKGROUND ART

As is well known, intercostal catheters have a distal end which may be inserted into the plural cavity of a patient for maintaining a negative pressure in the plural cavity where required and/or to remove wound drainage fluid from a wound or surgical incision to aid the healing process.

In U.S. Pat. No. 3,295,527, an intercostal catheter is shown having a funnel-like proximal end formed at an angle to the longitudinal axis of the tube and which has a point at the proximal tip. The distal end is a blunt end normal to the axis of the tube and is provided with a plurality of drainage openings in the sidewall adjacent the distal end. The proximal end may serve as a tube connector for connecting tubing to a drainage collection system that may include a source of suction. Where a surgical incision has been made for performing surgery, the proximal end is generally inserted through the surgical incision and then pulled, such as with forceps, through a secondary incision to the exterior of the patient until the distal end moves into the desired location within the patient. As the forceps pull the proximal end through the second incision, the open proximal end of the catheter tends to close reducing damage to the patient. The proximal end of the cath ter is formed in accordance with that patent by placing the tubing from which it is formed in a clamp, pressing the tube flat, and then cutting at the desired angle.

In cases where the chest of the patient is closed, for example, where there has been no incision into the plural cavity or open chest surgery but where there has been a puncture of the lung or other internal damage, such as due to an accident, the distal end of an intercostal catheter can be pinched, such as by forceps or by the fingers, and forced or tunneled from the exterior of the patient through an entrance incision, such as a stab wound or incision which passes between the ribs of the patient. Such a catheter may be connected to a suction source to maintain the plural cavity at a negative pressure to allow the lung to expand for breathing and so that fluid can readily drain from the wound.

Where the distal end of the catheter has a blunt end or is formed normal to the longitudinal axis of the tube, and is squeezed by the fingers or by forceps and moved into the incision from the exterior of the patient, the opposed sides of the substantially flattened end tend to increase in size and present a wide tube end extending normal to the tube axis. As a result, the catheter tends to tear or otherwise damage flesh during its movement through the incision into its desired location within the patient. In some other catheter constructions, undesirable protuberances occur when the distal end of the intercostal catheter is flattened during insertion.

Trocar catheters have also been used for closed-chest drainage. However, insertion of the catheter and pointed trocar into the patient has the potential danger of damaging the patient, such as piercing the lung, as a result of the insertion technique.

DISCLOSURE OF THE INVENTION

It is therefore an object of the present invention to provide an improved catheter having a distal end for insertion into an incision wherein the distal end is shaped to reduce or eliminate undesirable protuberances when flattened for insertion.

Another object of the present invention is to provide an intercostal catheter having a distal end with a shape which when laterally compressed can be readily inserted into an incision of a patient from the exterior of the patient with minimal traumatic effects.

Still another object of the present invention is to provide an improved method of making a catheter of the above type.

Still another object of the present invention is to provide an intercostal catheter and method of making the same which substantially avoids one or more of the above mentioned problems or disadvantages associated with prior art devices.

In accordance with one aspect of the invention, a method of making a catheter is provided which includes the steps of severing flexible tubing including cutting the tubing at an angle to the longitudinal axis of the tubing to form a distal end wall that has a distal tip, and a proximal end wall portion inclined radially inwardly. A part of the proximal wall portion is displaced to substantially prevent the proximal wall portion from extending distally beyond the outer edge of the end wall when the distal end portion is flattened for insertion into a patient. In accordance with another aspect of the invention, an intercostal catheter is provided which is made in accordance with the above-mentioned method.

These, as well as other objects and advantages of the present invention, will become apparent from the following detailed description and accompanying drawings.

BRIEF DESCRIPTION OF THE DRAWINGS

FIG. 1 is a top view of an intercostal catheter made in accordance with the present invention;

FIGS. 2–4 are illustrations of cutting steps employed in the manufacture of the catheter of FIG. 1;

FIG. 5 is a longitudinal cross-sectional side view, on an enlarged scale, of the distal end portion of the tubing subsequent to the cutting step of FIG. 4;

FIG. 6 is a bottom plan view of the distal end portion of the tubing of FIG. 5;

DETAILED DESCRIPTION OF THE PREFERRED EMBODIMENT

Figure 7:
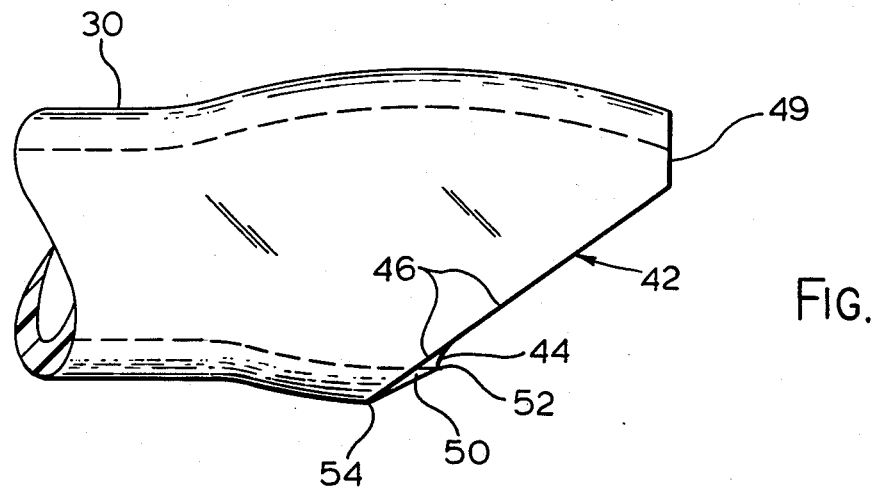
FIG. 7 is a side view of the tubing shown in FIGS. 5 and 6 but with opposed sides clamped together for purpose of explanation.

Referring now to the drawings and particularly of FIG. 1, an intercostal catheter 10 is shown including a flexible tube 12 having a proximal end portion 14 and a distal end portion 16. Tube 12 may be formed of a suitable, resilient and flexible material such as natural or synthetic rubber, a thermosetting plastic, or a thermoplastic. Preferably, the tube 12 is an extrusion formed of a thermoplastic material such as a plastisized polyvinyl chloride or the like. Preferably the tube is formed of a clear or transparent plastic.

The proximal end portion 14 is shown as being tapered with an end opening 17 and a surrounding proximal end wall 18 generally in a plane at an acute angle, for example, 20° to the center line or longitudinal axis of the tube. The end wall 18 is generally eliptical as viewed in FIG. 1. The tube 12 may be formed from extruded tubing having a smoothly curving enlarged portion which may be cut at an angle such as by use of a knife. The tapered proximal end 14 serves as a tube connector so that a tube such as a suction tube or tube connector (not shown) can be inserted into the tapered proximal end and frictionally connected in fluid tight sealing engagement with catheter 10. Except for the enlarged proximal end portion, the tube 12 is of substantially constant diameter. The proximal end portion 14 may be made if desired in accordance with the clamping and cutting steps disclosed in U.S. Pat. No. 3,295,527. In cases where open chest surgery has been performed, the proximal end 14 may be inserted into the original incision and pulled through a secondary incision to place the distal end portion 16 at the desired location within the patient.

The present invention is especially concerned with the distal end portion 16 of catheter 10. Distal end 16 has a distal end opening 20 and end wall 22 which includes a generally eliptical portion 24 generally in a plane at an acute angle to the longitudinal axis of the tube 12, and an arcuate tip portion 26 which is in a plane generally normal to the tube axis. A plurality of drainage holes 28 are provided in the sidewall of the tube 12 near the distal opening 20. The distal arcuate tip 26 provides a leading end which is stiffer and resists bending to greater extent than would a pointed tip like that at the proximal end 14.

The distal end portion 16 is adapted to be inserted from the exterior of the patient into a catheter insertion incision, such as a stab wound, and into the desired internal area such as the pleural cavity of the patient for the purpose of providing a negative pressure in the pleural cavity and/or draining fluid from the patient to enhance healing. Insertion of catheter 10 is performed in this manner especially in the case of closed chest drainage where no primary surgical incision has been made for performing an operation. The insertion of the catheter 10 by inserting the distal end 16 into the pateint from the exterior of the patient may, of course, be performed, if desired, even if there is a primary surgical incision. The distal end portion 16 is formed in accordance with the present invention such that it can be inserted into an incision in a patient with minimal trauma or damage to the patient, as will be discussed hereafter.

Referring now to FIG. 2, in the manufacture of catheter 10, tubing such as extruded polyvinyl chloride tubing, indicated at 30, and having a lumen 31, is placed on a platen or chopping board 32 below a vertically reciprocal knife or chopping blade 34. The bottom cutting edge of blade 34 and the longitudinal axis of tubing 30 are angularly related so that the blade will cut through the tubing, for example, in a plane including a line 36 in FIG. 3. Line 36 is in a plane at an acute angle, such as an angle of 35° with respect to the longitudinal axis of the tubing 30. The knife 34, when actuated, comes down and engages and partially flattens the tubing 30 which is supported by the platen by moving one side of the tubing toward the other along the cutting line and cuts through the tubing. Tubing 30 is thus severed by a chopping action, the knife passing through and engaging the platen. The tubing 30 then appears as shown in FIG. 4. The tubing may also be cut by the knife 34 or by any other suitable means in a plane including the line indicated at 38 in FIG. 4. Line 38 is in a plane normal to the longitudinal axis of tubing 30. As indicated in FIG. 4, the tubing is cut through to remove a pointed distal tip portion 40 from the tubing. In some cases both angular and normal cuts may be performed by a suitably shaped blade. The thus far processed distal end portion of tubing 30 is illustrated in FIGS. 5-7.

As seen FIGS. 5 and 6, the distal end portion of tubing 30, subsequent to the cutting steps indicated in FIGS. 3 and 4 has an end wall indicated generally at 42 which has radially inner and outer edges 44 and 46. End wall 42 includes a somewhat eliptical end wall portion 48 which is generally in a plane at an angle to the longitudinal axis of the tubing 30, and a blunt acurate tip end wall portion 49 in a plane generally normal to the axis of the tubing and which connects with the end wall portion 48. The end wall 42 terminates at the proximal end thereof.in a heel or proximal end wall portion 50 which is inclined radially inwardly and distally from the outer surface of tubing 30. The most proximal points on the inner and outer edges 44 and 46 are indicated, respectively, at 52 and 54 and are at the inner and outer surfaces, respectively, of tubing 30. The end wall 42 has a pair of opposed side wall portions 56 and 58 which are connected between the heel 50 and tip 49.

Figure 8:
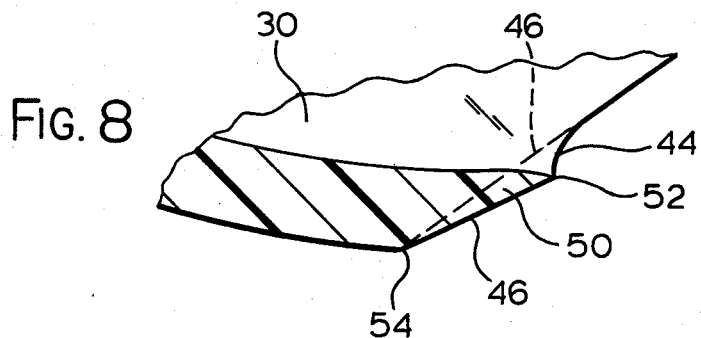
FIG. 8 is a fragmentary longitudinal cross-sectional view, on an enlarged scale, of the tubing shown in FIG. 7.

For purposes of illustration only, the distal end of tubing 30 is shown in FIG. 7 substantially flattened as a result of the application of forces to the opposed sides of the tubing shown in FIGS. 5 and 6, for example, by arms 60 and 62 of a clamp or forceps and by the forces as indicated by the arrows in FIG. 6. As the distal end of the tubing is flattened, the most proximal point 52 on the inner edge 44 of the end wall 42 moves generally distally outwardly, so that a protuberance of the end wall 42 is produced as indicated in FIGS. 7 and 8. The protuberance is formed by a portion of the heel 50 of the end wall 42 protruding beyond the outer edge 46 of the end wall 42 while the opposed side wall portions 56 and 58 of the end wall are approximately in the same plane. As seen in FIGS. 7 and 8, a portion of inner edge 44, the most proximal point 52 of the inner edge 44, and a small surface of the lumen 31 protrude distally beyond the outer edge 46. This protuberance occurs when the opposed sides of the tube adjacent the heel 50 are forced together with tube being creased or folded at the line 64 in FIG. 6. Line 64 is at the outer surface of the tubing 30 and intersects the most proximal points 52 and 54 of the inner and outer edges dividing the tubing end in symmetrical halves. The most proximal point 52 of the inner edge is shown in longitudinal alignment with point 54 but is radially inwardly thereof. This protuerance occurs if the tubing is similary pinched at the heel 50 between the thumb and a finger.

It is seen from FIG. 7 that if the tubing 30 thus far processed was flattened at the heel 50 by creasing at line 64, and then inserted into an incision from the exterior of the patient, that the protuberance of the heel 50 would act as a barb and could produce deleterious effects on th flesh of the patient. However, in accordance with the present invention, an intercostal catheter is made so that it is free of such a protuberance so that the catheter may be pinched or flattened at the heel and passed through an incision without coring or tearing flesh and in general with minimal trauma or deleterious effects to patient. This is accomplished by reshaping, or displacing a portion of the distal end of tubing 30, or removing a part of the proximal portion of the distal end wall, as will be discussed herein.

In providing an intercostal catheter without a heel protuberance or deleterious barb, such as indicated in FIGS. 7 and 8, a portion of the heel 50 is displaced from the distal end of the tubing. For purposes of illustration and understanding, the tubing material displaced is indicated in FIGS. 5 and 6 between the inner edge 44 and a dashed line 70. In effect, the most proximal point of the inner edge 44 is moved proximally to the dashed line 70 as indicated by a point 72 in FIGS. 5 and 6. In this way, the slope or incline of the new heel 50 is increased and especially between points 54 and 72. By moving the proximal extremity of the end wall inner edge proximally, when the distal end portion of tubing 30 is pinched or flattened by opposing forces such as indicated by the arrows in FIG. 6, no protuberance is formed. This is because the new proximal extremity of the end wall and the new inner edge including point 72 will not extend distally beyond the outer edge 46 of the end wall upon being compressed or flattened and creased on line 64.

Preferably, the material of the heel 50 is displaced by melting the plastic material of the heel 50 and distributing it along the tubing. In the preferred illustrated embodiment, the distal end of tubing 30 is inserted into a heated melt mold illustrated embodiment, the distal end of tubing 30 is inserted into a heated melt mold such as indicated at 75 in FIG. 9 which not only displaces a portion of heel 50 to prevent the protuberance but also radiuses or rounds the sharp edges resulting from severing the tubing 30.

Figure 9:
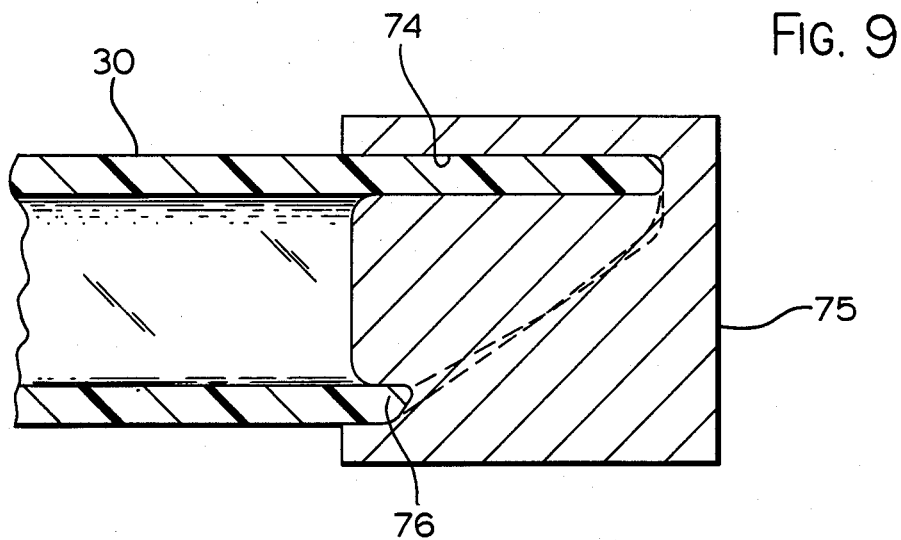
FIG. 9 is an illustration of another step in the process of making the catheter of FIG. 1.

As seen in FIG. 9, the tubing, after being removed from the mold 75, flattened and creased longitudinally at the proximal most points on the new heel 76 (such as along a line 64, FIG. 6), has no protuberance at the distal end of the tubing. The mold 75, as will be apparent to those skilled in the art, is formed so that as the distal end of tubing 30 moves into the heated mold, the material will flow from the heel area and be spread out onto other surfaces.

Figure 10:
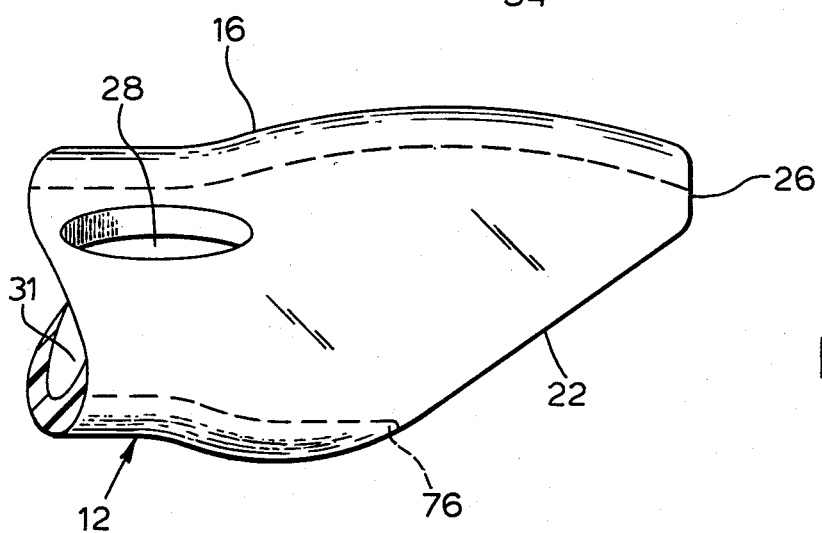
FIG. 10 is a side view illustrating the of the distal end portion of the tubing subsequent to the step illustrated in FIG. 9 but with the distal end of the tubing flattened.
Figure 11:
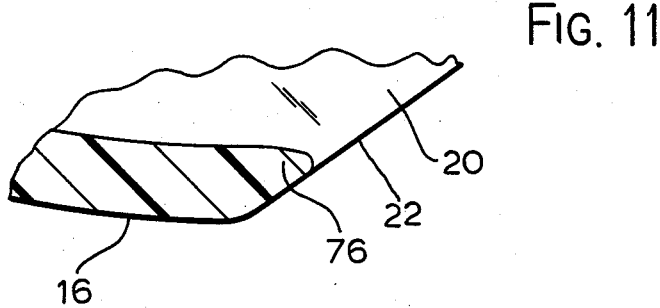
FIG. 11 is a fragmentary longitudinal cross-sectional view, on an enlarged scale, of the tubing shown in FIG. 10.

The step indicated in FIG. 9 not only simultaneously results in a catheter free of the protuberance or barb indicated in FIG. 7, but efficiently also removes the sharp edges and provides a radius on all sharp edges. Removal of sharp edges, of course, reduces tissue damage. The distal end portion of the tube may be provided with sidewall fluid drainage openings 28, as shown in FIGS. 1 and 10, by conventional or suitable punching apparatus well known to those in the art. The distal end 16 of FIG. 10 is the same distal end of tubing 30 of FIG. 7 but after the melt-molding step indicated in FIG. 9 and after openings 28 have been made. Thus, a distal end portion shown in FIG. 10 is the finished distal end of the catheter 10 of FIG. 1 but in the pinched or flattened condition ready for insertion into an incision from the exterior of the patient. It is seen in FIG. 10 that no protrusion or barb extends distally from the distal end wall 22 of the catheter when the catheter is pinched or folded at the heel. As seen also from FIG. 11, the new heel, indicated at 76, moves distally but not distally past the distal end of the tube when the distal end is flattened or pinched at the heel.

The intercostal catheter 10 of FIG. 1 can thus be utilized for both open and closed chest drainage situations. For Example, as pointed out previously the proximal end 14 of catheter 10 may be pulled through a secondary incision from the interior of the patient when there is an original incision by means of a forceps. Catheter 10, on the other hand, may be used where it is desired to collapse or flatten the distal end 16 by forceps or fingers and pass the distal end into an incision from the exterior of the patient to a desired position within the patient. The inclined distal end portion 22 of the catheter 10 aids in passing the end through an incision while the blunt tip 26 resists bending that might otherwise interfere with insertion.

Severing plastic tubing by chopping it as shown and described herein is quick and easy so that it is an economical method of severing. Generally, such chopping produces a tube that has a protrusion like that shown in FIGS. 7 and 8 and which is readily avoided in the final product by displacing or removing the heel portion of the distal end opening or end wall as described herein. The severing of the tube can also be performed by a scissors or a scissors-like cutting device. Severing the tubing by chopping or by use of a scissors generally produces a heel tha results in an undesirable protuberance but which can be eliminated or reduced by suitable heat melting in accordance with this invention.

As various changes could be made in the above described construction and method without departing from the true spirit and scope of the invention, it is intended that all matter contained in the above description and shown in the accompanying drawings be interpreted as illustrative.

What is claimed is:

1. In a method of making a catheter, the steps of severing resilient flexible tubing including cutting the tubing generally in a plane at an angle to the longitudinal axis of the tubing to effect a distal end wall having a distal tip, a proximal wall porfion, and a pair of opposed sidewalls connecting the distal tip with the proximal wall portion, and such that the proximal wall portion protrudes distally beyond the dista end of the tubing when the opposed end walls are pinched together adjacent the proximal end wall portion, and the tubing being in a substantially unflattened state at the cutting site when said step of severing is initiated, displacing a sufficient part of the proximal wall portion to substantially prevent the proximal wall portion from protruding distally beyond the distal end of the tubing when the sidewalls are pinched together adjacent the proximal end wall portion.

2. The method of claim 1 wherein said step of displacing a sufficient part of the proximal wall portion includes the step of melt-forming a part of the proximal wall portion.

3. The method of claim 2 wherein said tubing has a constant diameter portion, and said step of severing the flexible tubing is made by chopping the tubing in the constant diameter portion with a cutting element while the tubing is on a platen.

4. The method of claim 2 wherein said step of melt-forming includes providing a melt-forming mold, and inserting the distal end of the tubing into the mold, the mold being shaped to displace the sufficient part of the proximal wall portion.

5. The method of claim 4 wherein said mold is shaped to further effect rounding of all edges of the distal end of the tubing by melting the edges during insertion of the distal end of the tubing in the mold.

6. The method of claim 5 wherein said cutting of the tubing is made by chopping the tubing with a cutting element while on a platen.

7. In a method of making an intercostal catheter having a distal end wall adapted to be inserted into an incision in a patient from the exterior of the patient, the steps of severing resilient flexible tubing including cutting the tubing in a plane at an angle to the longitudinal axis of the tubing to effect a distal end wall having radially inner and outer edges and defining a distal end opening, the distal end wall having a distal tip, a proximal end wall portion inclined radially inwardly, and opposed side wall portions connected between the distal tip and the tubing being in a substantially unflattened state at the cutting site when said step of severing is initiated, proximal end wall portion, the proximal end wall portion being invertible in response to the substantial flattening of the distal end of the tubing by movement of the opposed sidewall portions together with the tubing creased longitudinally at the most proximal point on the outer edge to thereby effect a protruding part of the proximal end wall portion that etends distally outwardly beyond the outer edge of the end wall, and displacing a sufficient portion of the proximal end wall portion to substantially prevent the proximal end wall portion from extending beyond the outer edge when the distal end of the tubing is similarly flattened.

8. The method of claim 7 wherein said displacing step includes melting a portion of the proximal end wall portion.

9. The method of claim 8 wherein said melting step includes inserting the distal end of the tubing in a heated mold.

10. The method of claim 9 wherein said severing step comprises chopping the tubing on a platen.

11. The method of claim 9 wherein all sharp edges are rounded by melting during said insertion of the distal end in the mold.

12. The method of claim 7 wherein the tubing has an enlarged tapered portion, and includes the step of cutting through the tapered portion to provide an open tube connector at the proximal end of the tubing.

13. An intercostal catheter made according to claim 7.

14. The intercostal catheter of claim 13 further including a proximal open end tapered to serve as a tube connector.

15. The method of claim 1 wherein said cutting step includes placing the tubing in its normal unflattened state between a cutting blade and platen means, and moving the blade to engage a portion of the tubing while in the unflattened state and thereafter passing the blade through the tubing.

16. The method of claim 15 wherein the tubing is formed of a thermoplastic material.

17. The method of claim 8 wherein the tubing is formed of a thermoplastic maerial and is normally circular in cross-section.

* * * * *